(12) United States Patent
Nomoto et al.

(10) Patent No.: US 11,970,681 B2
(45) Date of Patent: Apr. 30, 2024

(54) PLATE (71) Applicant: Ushio Denki Kabushiki Kaisha, Tokyo (JP)

(72) Inventors: Daisuke Nomoto, Tokyo (JP); Makoto Yamanaka, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 677 days.

(21) Appl. No.: 17/261,466

(22) PCT Filed: Jul. 2, 2019

(86) PCT No.: PCT/JP2019/026310
§ 371 (c)(1),
(2) Date: Jan. 19, 2021

(87) PCT Pub. No.: WO2020/031556
PCT Pub. Date: Feb. 13, 2020

(65) Prior Publication Data
US 2021/0253988 A1  Aug. 19, 2021

(30) Foreign Application Priority Data
Aug. 7, 2018  (JP) .................................. 2018-148277

(51) Int. Cl.
*B01L 3/00* (2006.01)
*B81B 1/00* (2006.01)
(Continued)

(52) U.S. Cl.
CPC ............. *C12M 23/16* (2013.01); *B81B 1/006* (2013.01); *B81C 99/007* (2013.01); *C12M 23/12* (2013.01);
(Continued)

(58) Field of Classification Search
CPC . C12M 23/50; B01L 2300/021; B81C 99/007
See application file for complete search history.

(56) References Cited

U.S. PATENT DOCUMENTS

| 7,582,261 | B2 | 9/2009 | Fuji | |
|---|---|---|---|---|
| 2006/0039829 | A1* | 2/2006 | Suk | ................... B01L 3/502746 204/601 |

(Continued)

FOREIGN PATENT DOCUMENTS

| JP | 2005-147954 A | 6/2005 |
|---|---|---|
| JP | 2005-164296 A | 6/2005 |

(Continued)

OTHER PUBLICATIONS

Office Action dated Jul. 31, 2023 for CN Application No. 201980051086.1, which corresponds to the current U.S. Appl. No. 17/261,466.

*Primary Examiner* — Nathan A Bowers
(74) *Attorney, Agent, or Firm* — Kenichiro Yoshida (57) ABSTRACT

To provide a plate with which, although the plate has a plurality of microchannels or a microchannel in which a plurality of branch channels are formed, when a sample flowing through a microchannel is observed by a microscope, it is possible to easily identify the position of the microchannel or the branch channel under observation without reducing the magnification of the microscope.

A plate having a microchannel therein includes an identification mark for identifying a position of the microchannel in a plane direction of the plate. When the microchannel includes a plurality of mutually independent microchannels, the identification mark is preferably formed for each microchannel. When the microchannel includes a source channel communicating with an injection port through which a sample is injected and a plurality of branch channels com-
(Continued)

municating with the source channel, the identification mark is preferably formed for each of the source channel and the branch channels.

7 Claims, 4 Drawing Sheets

(51) Int. Cl.
  *B81C 99/00* (2010.01)
  *C12M 1/00* (2006.01)
  *C12M 1/32* (2006.01)
  *C12M 3/06* (2006.01)
(52) U.S. Cl.
  CPC ......... *C12M 23/50* (2013.01); *B81B 2201/05* (2013.01); *B81B 2203/0338* (2013.01)

(56) References Cited

U.S. PATENT DOCUMENTS

| | | | |
|---|---|---|---|
| 2008/0153152 A1* | 6/2008 | Wakabayashi | B01F 25/4338 435/287.2 |
| 2009/0299545 A1* | 12/2009 | Quan | B01L 3/502707 382/141 |
| 2015/0202625 A1* | 7/2015 | Hong | B81C 99/0095 156/248 |
| 2017/0031330 A1* | 2/2017 | Shiraishi | G06N 7/01 |
| 2018/0071736 A1 | 3/2018 | Qin et al. | |

FOREIGN PATENT DOCUMENTS

| | | |
|---|---|---|
| JP | 2008-151771 A | 7/2008 |
| JP | 2016-26904 A | 2/2016 |
| JP | 2018-47614 A | 3/2018 |

\* cited by examiner

PLATE

TECHNICAL FIELD

The present invention relates to a plate having a microchannel therein, and more specifically relates to a plate suitable as a culture vessel in which a cell or a biological tissue can be observed while being cultured in a microchannel.

BACKGROUND ART

Functions of cells are controlled in an extracellular microenvironment in a living body. In this case, the extracellular microenvironment includes soluble factors, such as growth factors, vitamins, and gas molecules; insoluble factors, such as extracellular matrix; and cell-cell interactions.

Conventionally, a culture vessel, such as a culture dish or a culture plate, on which a culture medium such as agar is formed has been used for culturing cells or biological tissues. Since cell culture using such a culture vessel is performed in a two-dimensional (planar) environment, it is difficult to reproduce the extracellular microenvironment. Under such circumstances, a plate (a biochip, a microchip) having a microchannel capable of cell culture in a three-dimensional (stereoscopic) environment has been proposed (see PTL 1).

Figure 13:
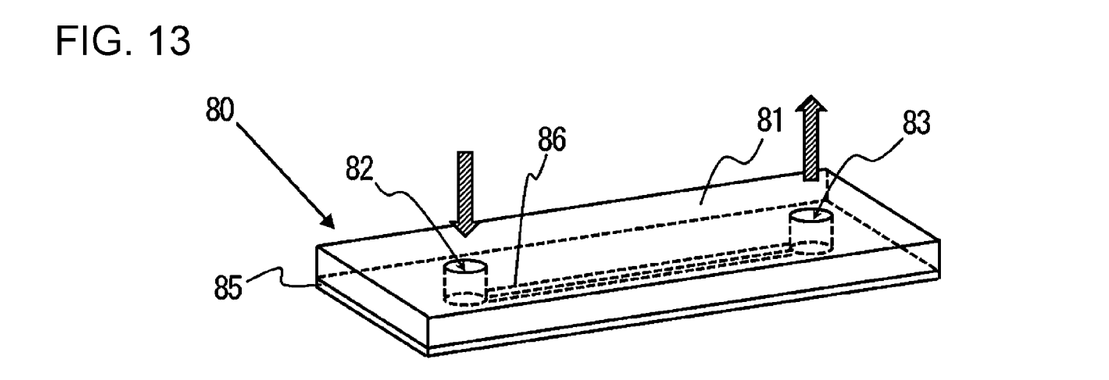
FIG. 13 is an explanatory view illustrating a configuration of an example of a conventional plate.

FIG. 13 is an explanatory view illustrating a configuration of an example of a conventional plate. The plate 80 is constituted by integrally bonding a transparent first substrate 81 having an injection port 82 through which a liquid sample is injected and a discharge port 83 through which the liquid sample is discharged, and a second substrate 85 stacked on the first substrate 81. A microchannel 86 extending from the injection port 82 toward the discharge port 83 is formed inside the plate 80.

In the plate 80, the liquid sample injected from the injection port 82 flows through the microchannel 86 and then is discharged from the discharge port 83. When the liquid sample flows through the microchannel 86, the state of cells or the like in the liquid sample can be magnified and observed by a microscope.

However, when such a plate has a plurality of microchannels or a microchannel in which a plurality of branch channels are formed, there are problems as follows.

In some cases, it is difficult to determine the microchannel or branch channel that is currently observed in the middle of magnifying and observing cells or the like in a liquid sample flowing through a microchannel by a microscope. In such a case, it is necessary to temporarily reduce the magnification of the microscope, identify the position of the channel being observed, then increase the magnification of the microscope, and continue the observation of the cells or the like again.

Such an operation is very complicated, and particularly in a case where several tens to several hundreds of fine microchannels are arranged at high density, even when the magnification of the microscope is reduced, it is difficult to identify the microchannel being observed.

CITATION LIST

Patent Literature

PTL 1: Japanese Laid-open Patent Publication No. 2018-47614

SUMMARY OF INVENTION

Technical Problem

An object of the present invention is to provide a plate with which, although the plate has a plurality of microchannels or a microchannel in which a plurality of branch channels are formed, when a sample flowing through a microchannel is observed by a microscope, it is possible to easily identify the position of the microchannel or the branch channel under observation without reducing the magnification of the microscope.

Solution to Problem

A plate according to the present invention is a plate having a microchannel therein, the plate including an identification mark for identifying a position of the microchannel in a plane direction of the plate.

In the plate according to the present invention, the microchannel preferably includes a plurality of microchannels formed independently from each other, and the identification mark is preferably formed for each of the microchannels.

Also, in the plate according to the present invention, the microchannel preferably includes a source channel communicating with an injection port through which a sample is injected and a plurality of branch channels communicating with the source channel, and the identification mark is preferably formed for each of the source channel and the branch channels.

Also, in the plate according to the present invention, the identification mark is preferably formed in an area near the microchannel or an area overlapping with the microchannel when seen in a plan view.

Also, in the plate according to the present invention, the plate preferably includes a first substrate in which a channel forming groove for forming the microchannel is formed and a second substrate stacked on the first substrate, the first substrate and the second substrate being bonded to each other, and the first substrate is preferably made of a transparent synthetic resin.

Also, the synthetic resin is more preferably made of a cycloolefin resin.

Also, the identification mark is preferably formed in or on a surface of the first substrate to be bonded to the second substrate, a surface of the second substrate 15 to be bonded to the first substrate, or both of the surfaces.

Also, a weld line may be formed through injection molding in the first substrate, and the identification mark may include the weld line.

Also, in the plate according to the present invention, the identification mark may include a one-dimensional code or a two-dimensional code.

Advantageous Effects of Invention

According to the plate of the present invention, since the identification mark for identifying the position of the microchannel in the plane direction is formed, although the plate has the plurality of microchannels or the microchannel in which the plurality of branch channels are formed, when a sample flowing through a microchannel is observed by a microscope, it is possible to easily identify the position of the microchannel or the branch channel under observation without reducing the magnification of the microscope.

DESCRIPTION OF EMBODIMENTS

Hereafter, embodiments of a plate of the present invention will be described.

First Embodiment

Figure 1:
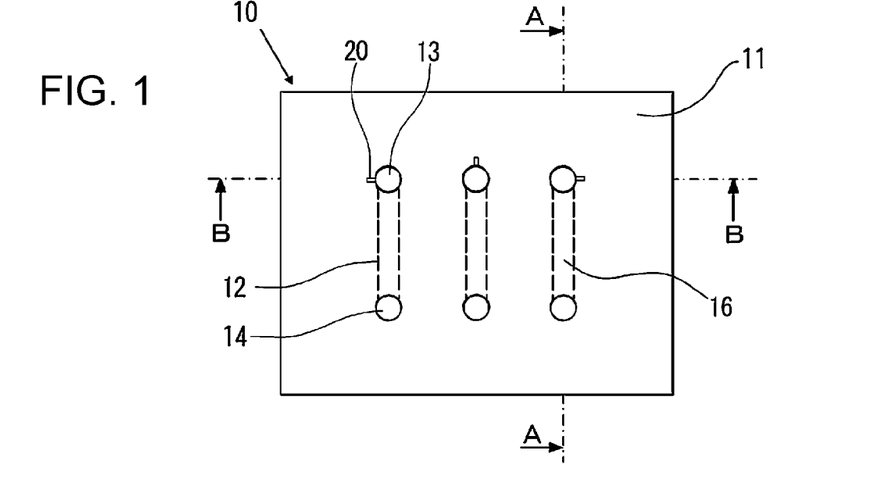
FIG. 1 is a plan view illustrating a configuration of a plate according to a first embodiment of the present invention.
Figure 2:
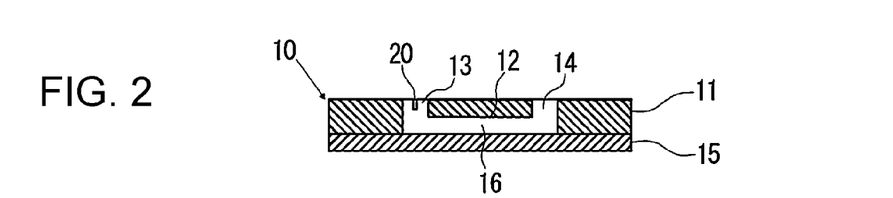
FIG. 2 is a sectional view taken along line A-A of the plate illustrated in FIG. 1.
Figure 3:
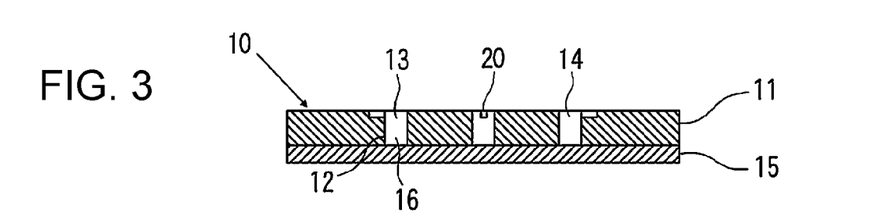
FIG. 3 is a sectional view taken along line B-B of the plate illustrated in FIG. 1.

FIG. 1 is a plan view illustrating a configuration of a plate according to a first embodiment of the present invention. FIG. 2 is a sectional view taken along line A-A of the plate illustrated in FIG. 1. FIG. 3 is a sectional view taken along line B-B of the plate illustrated in FIG. 1.

The plate 10 is constituted by a plate-shaped body in which a transparent first substrate 11 and a second substrate 15 are stacked and integrally bonded. The plate 10 of this example has a plurality of (in the illustrated example, three) linear microchannels 16 therein. These microchannels 16 are formed independently without communicating with each other, and are arranged in parallel.

In the first substrate 11, a channel forming groove 12 is formed in a surface (a lower surface in FIG. 2) on a side in contact with the second substrate 15. In contrast, a surface (an upper surface in FIG. 2) of the second substrate 15 on a side in contact with the first substrate 11 is a flat surface. The channel forming groove 12 formed in the first substrate 11 forms the microchannel 16 between the first substrate 11 and the second substrate 15.

In addition, an injection port 13 through which a liquid sample is injected and a discharge port 14 through which the liquid sample is discharged are formed in the first substrate 11 to extend through the first substrate 11 in the thickness direction to correspond to each microchannel 16. One end of each of the microchannels 16 is connected in communication with the corresponding injection port 13, and one end of each of the microchannels 16 is connected in communication with the corresponding discharge port 14.

The plate 10 of the present invention has an identification mark 20 for identifying the position of the microchannel 16 in the plane direction of the plate 10. The identification mark 20 in or on the plate 10 of the illustrated example is formed in an area near the microchannel 16 in the first substrate 11 for each microchannel 16 when the plate 10 is seen in a plan view. Specifically, each of the identification marks 20 is constituted by a recess provided around each of the injection ports 13 in the surface of the first substrate 11. These identification marks 20 are each provided for identifying the position of the corresponding microchannel 16 in the plane direction of the plate 10 by the difference in the relative position of the recess with respect to the injection port 13.

Describing with reference to FIG. 1, the identification mark 20 relating to the microchannel 16 located on the left side is formed at a position on the left side of the opening of the injection port 13 in the drawing to extend in the radial direction of the opening. Also, the identification mark 20 relating to the microchannel 16 located at the center is formed at a position on the upper side of the opening of the injection port 13 in the drawing to extend in the radial direction of the opening. Also, the identification mark 20 relating to the microchannel 16 located on the right side is formed at a position on the right side of the opening of the injection port 13 in the drawing to extend in the radial direction of the opening. In this way, the position of the microchannel 16 relating to an identification mark 20 in the plane direction of the plate 10 is identified by the difference in the position of the identification mark 20 with respect to the opening of the injection port 13, and consequently, the microchannel 16 is distinguished from the microchannel 16 relating to another identification mark 20.

As a material constituting the first substrate 11, a transparent synthetic resin can be used. Specific examples of the synthetic resin include a silicone resin such as polydimethylsiloxane, a cycloolefin resin, and an acrylic resin.

Among these examples, the cycloolefin resin is preferably used in the viewpoint of injection moldability, transparency, strength, bondability, and so forth.

As a material constituting the second substrate 11, a synthetic resin can be used, and specific examples thereof include those similar to the synthetic resin constituting the first substrate 11.

The thickness of each of the first substrate 11 and the second substrate 15 is not particularly limited, and is, for example, 0.5 to 7 mm. The width of the microchannel 16 is, for example, 0.1 to 3 mm. The height of the microchannel 16 (the depth of the channel forming groove 12) is, for example, 0.05 to 1 mm.

The above-described plate 10 can be manufactured, for example, as follows.

First, as illustrated in FIG. 3, the first substrate 11 and the second substrate 15 made of resin are manufactured. The channel forming groove 12 is formed in the surface of the first substrate 11, and the injection port 13 and the discharge port 14 extending through the first substrate 11 in the thickness direction are formed at both end positions of the channel forming groove 12. In contrast, the surface of the second substrate 15 is a flat surface.

As a method of manufacturing the first substrate 11 and the second substrate 15, a resin molding method, such as an injection molding method or a casting method, can be appropriately selected in accordance with the resin to be used.

Then, a surface activation treatment is applied to a surface to be a bonding surface of each of the first substrate 11 and the second substrate 15. As the surface activation treatment, an ultraviolet irradiation treatment of irradiating the surface with vacuum ultraviolet rays having a wavelength of 200 nm or less, or a plasma treatment of bringing atmospheric plasma from an atmospheric plasma apparatus into contact with the surface can be used.

When the ultraviolet irradiation treatment is used as the surface activation treatment, an excimer lamp such as a xenon excimer lamp having emission lines with a wavelength of 172 nm, a low-pressure mercury lamp with a center wavelength of 185 nm, or a deuterium lamp having a strong emission spectrum with a wavelength in a range of 120 to 200 nm can be suitably used as a light source for emitting vacuum ultraviolet rays.

The irradiance of the vacuum ultraviolet rays emitted on the surface of each of the first substrate 11 and the second substrate 15 is, for example, 5 to 500 mW/cm$^2$.

The irradiation period of time with the vacuum ultraviolet rays to the surface of each of the first substrate 11 and the second substrate 15 is appropriately set in accordance with the resin constituting the first substrate 11 and the second substrate 15, and is, for example, 5 to 6 seconds.

When the plasma treatment is used as the surface activation treatment, it is preferable to use, as a plasma generation gas, a gas containing nitrogen gas, argon gas, or the like as a main component and containing 0.01% to 5% by volume of oxygen gas. Alternatively, a mixed gas of nitrogen gas and clean dry air (CDA) can be used.

The operating conditions of the atmospheric plasma apparatus used for the plasma treatment are, for example, a frequency of 20 to 70 kHz, a voltage of 5 to 15 kVp-p, and a power value of 0.5 to 2 kW.

The treatment period of time with the atmospheric plasma is, for example, 5 to 100 seconds.

The first substrate 11 and the second substrate 15 subjected to the surface activation treatment as described above are stacked such that the surfaces thereof are in contact with each other. Then, the first substrate 11 and the second substrate 15 are bonded to each other in a state where the first substrate 11 and the second substrate 15 are pressed in the thickness direction by their own weight or by applying pressure from the outside by heating as necessary.

In the above description, specific conditions of the pressing and heating are appropriately set in accordance with the material constituting the first substrate 11 and the second substrate 15.

Specific conditions include a pressing force of, for example, 0.1 to 10 MPa and a heating temperature of, for example, 40° C. to 150° C.

As described above, the identification mark 20 in the first substrate 11 can be directly formed by a resin molding method, such as an injection molding method or a casting method. Alternatively, the first substrate 11 having the identification mark 20 may be fabricated by fabricating a molded body for the first substrate having no identification mark 20 formed therein by a resin molding method, and then forming a recess around each of the injection ports 13 in the surface of the first substrate 11 by mechanical processing.

Second Embodiment

Figure 4:
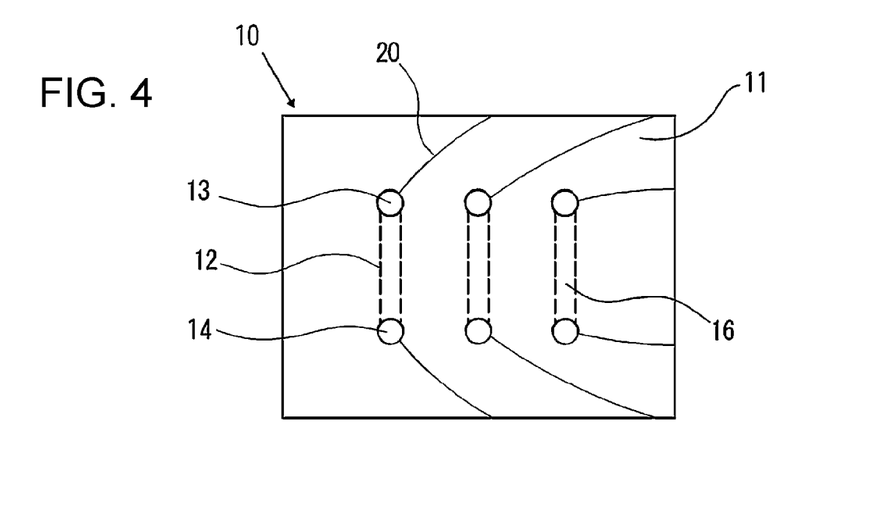
FIG. 4 is a plan view illustrating a configuration of a plate according to a second embodiment of the present invention.

FIG. 4 is a plan view illustrating a configuration of a plate according to a second embodiment of the present invention. Similarly to the plate 10 according to the first embodiment, the plate 10 is constituted by a plate-shaped body in which a transparent first substrate 11 and a second substrate 15 (see FIG. 2) are stacked and integrally bonded to each other, the first substrate 11 having a channel forming groove 12, an injection port 13, and a discharge port 14 formed therein. A plurality of (in the illustrated example, three) linear microchannels 16 are formed inside the plate 10 independently without communicating with each other and are arranged in parallel.

In the first substrate 11, weld lines formed through injection molding are formed so as to extend from the opening edges of the injection port 13 and the discharge port 14 to the peripheral edges of the first substrate 11 when the first substrate 11 is seen in a plan view. In this case, since the first substrate 11 has the injection port 13 and the discharge port 14 formed to extend though the first substrate 11 in the thickness direction, the weld lines are inevitably generated in the obtained first substrate 11 when the first substrate 11 is fabricated by injection molding with a thermoplastic synthetic resin.

In the plate 10 of this example, an identification mark 20 for identifying the position of a microchannel 16 in the plane direction of the plate 10 is formed for each microchannel 16 by a weld line formed in the first substrate 11. These identification marks 20 are each provided for identifying the position of the corresponding microchannel 16 in the plane direction of the plate 10 by the difference in the direction in which the weld line constituting the identification mark 20 extends. The direction in which the weld line extends can be adjusted by, for example, the position of a gate of a mold that is used for injection molding.

Other configurations of the plate 10 according to the second embodiment are similar to those of the plate 10 according to the first embodiment.

Third Embodiment

Figure 5:
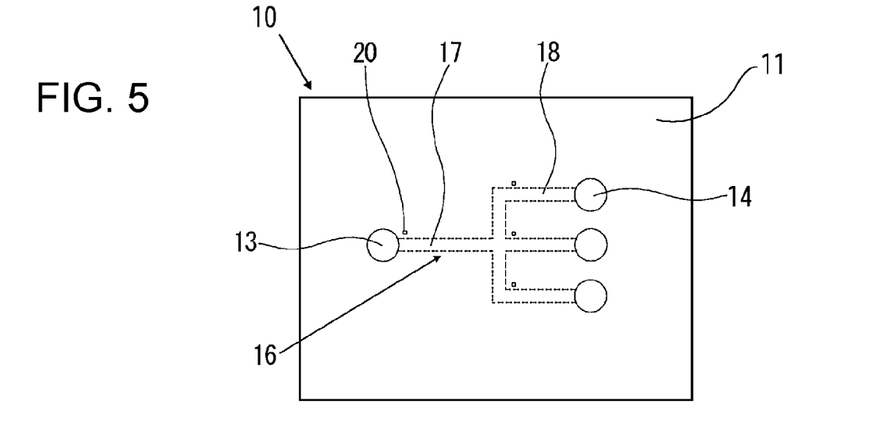
FIG. 5 is a plan view illustrating a configuration of a plate according to a third embodiment of the present invention.

FIG. 5 is a plan view illustrating a configuration of a plate according to a third embodiment of the present invention. Similarly to the plate 10 according to the first embodiment, the plate 10 is constituted by a plate-shaped body in which a transparent first substrate 11 and a second substrate 15 (see FIG. 2) are stacked and integrally bonded to each other, the first substrate 11 having a channel forming groove 12, an injection port 13, and a discharge port 14 formed therein. A microchannel 16 is formed inside the plate 10.

In the plate 10, the microchannel 16 includes a source channel 17 communicating with the injection port 13 and a plurality of (in the illustrated example, three) branch channels 18 communicating with the source channel 17. Each of the branch channels 18 is connected in communication with the discharge port 14 formed to correspond to the branch channel 18.

In addition, in the plate 10 of this example, when seen in a plan view, an identification mark 20 including a one-dimensional code or a two-dimensional code is formed in an area near each of the source channel 17 and the branch channels 18 in the first substrate 11. As the two-dimensional code, a QR code (registered trademark), a VeriCode, a DataMatrix, or the like can be used.

When a one-dimensional code or a two-dimensional code is used as the identification mark 20, information on, for example, a channel length can be recorded in addition to information for identifying the position of the microchannel 16 (the source channel 17 and the branch channels 18) in the plane direction of the plate.

Other configurations of the plate 10 according to the third embodiment are similar to those of the plate 10 according to the first embodiment.

As a method of forming the identification mark 20 including the one-dimensional code or the two-dimensional code in the first substrate 11, marking with laser light, machining, nanoimprinting, exposure to light, or the like can be used.

Fourth Embodiment

Figure 6:
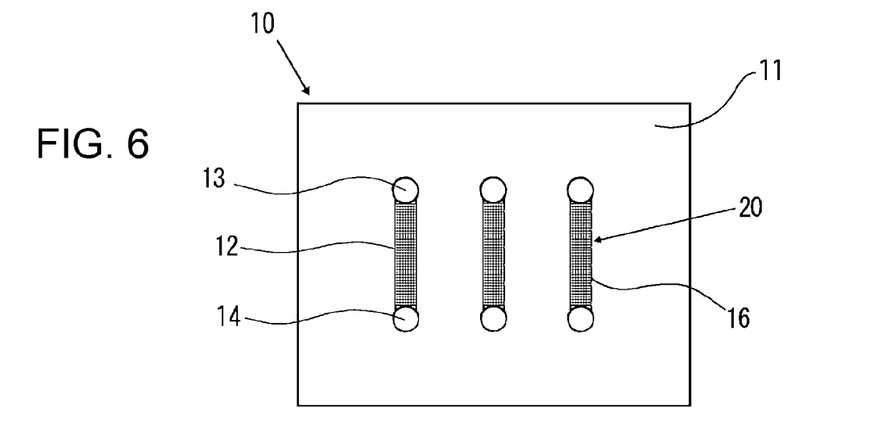
FIG. 6 is a plan view illustrating a configuration of a plate according to a fourth embodiment of the present invention.

FIG. 6 is a plan view illustrating a configuration of a plate according to a fourth embodiment of the present invention.

Similarly to the plate 10 according to the first embodiment, the plate 10 is constituted by a plate-shaped body in which a transparent first substrate 11 and a second substrate 15 (see FIG. 2) are stacked and integrally bonded to each other, the first substrate 11 having a channel forming groove 12, an injection port 13, and a discharge port 14 formed therein. A plurality of (in the illustrated example, three) linear microchannels 16 are formed inside the plate 10 independently without communicating with each other and are arranged in parallel.

Figure 7:
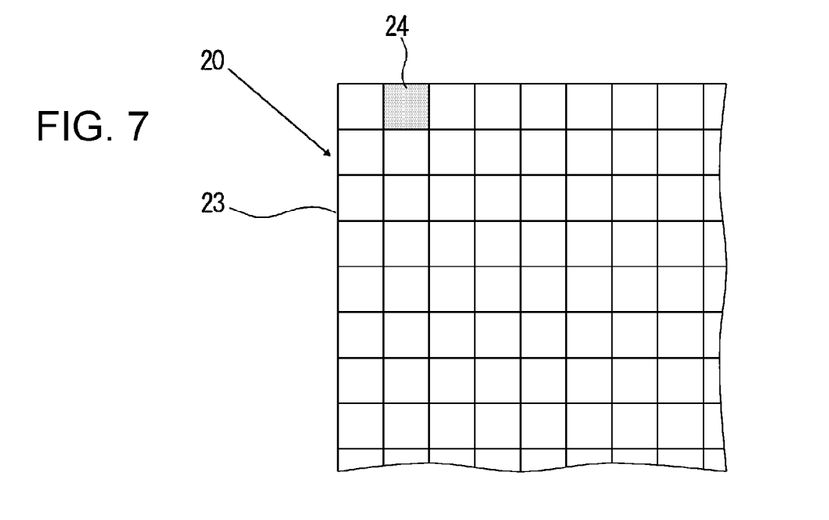
FIG. 7 is an enlarged explanatory view illustrating an identification mark on the plate illustrated in FIG. 6.

In the plate 10 of this example, an identification mark 20 is formed in each of areas of the first substrate 11 that overlap with the microchannels 16 when seen in a plan view. As illustrated in FIG. 7 in an enlarged manner, each of the identification marks 20 is constituted by a grid FIG. 23 and an opaque area 24 provided in a region of one cell in the grid FIG. 23. These identification marks 20 are each provided for identifying the position of the corresponding microchannel 16 in the plane direction of the plate 10 by the difference in the position of the opaque area 24 in the grid FIG. 23. The size of the cell in the grid FIG. 23 (the size of the surface of the opaque area 24) can be appropriately set in accordance with the number of the microchannels 16 and the size of the microchannels 16, and is, for example, a size of 1 μm×1 μm.

As a method of forming the grid FIG. 23 on the first substrate 11, marking with laser light, machining, nanoimprinting, exposure to light, or the like can be used.

As a method of forming the opaque area 24, it is possible to use a method of applying matte finish to the surface of the first substrate 11. As the matte finish, a blast treatment can be used.

With the plate 10 according to the above-described first to fourth embodiments, since the identification mark 20 for identifying the position of the microchannel 16 in the plane direction is formed, although the plate 10 has the plurality of microchannels 16 or the microchannel 16 having the plurality of branch channels 18, when a sample flowing through a microchannel 16 is observed by a microscope, it is possible to easily identify the position of the microchannel 16 or the branch channel 18 in the plate 10 without reducing the magnification of the microscope.

The plate of the present invention is not limited to the above-described embodiments, and various modifications can be made as follows.

(1) In the plate of the present invention, the identification mark is not limited to those of the first to fourth embodiments as long as the identification mark can be visually or optically recognized and can provide identification for the position of the microchannel in the plane direction of the plate.

Figure 8:
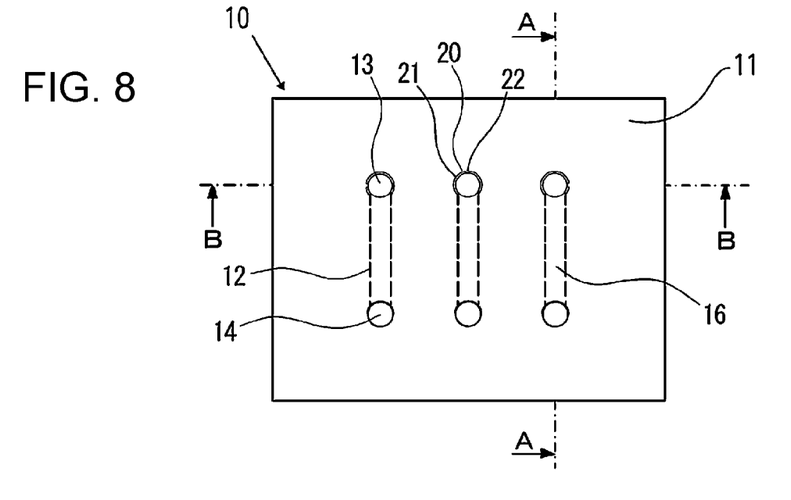
FIG. 8 is a plan view illustrating a modification of the plate of the present invention.
Figure 9:
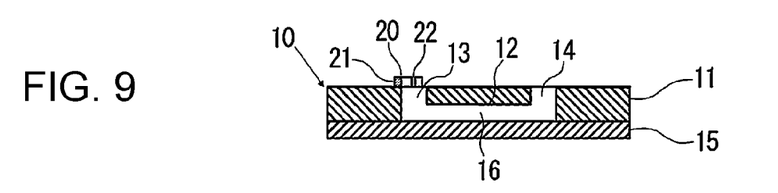
FIG. 9 is a sectional view taken along line A-A of the plate illustrated in FIG. 8.
Figure 10:
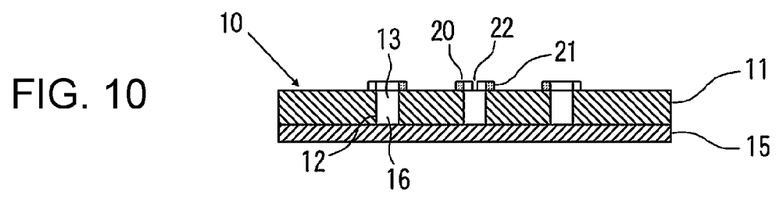
FIG. 10 is a sectional view taken along line B-B of the plate illustrated in FIG. 8.

For example, as illustrated in FIGS. 8 to 10, an identification mark 20 may be formed by a protruding portion 21 protruding from the outer surface of the first substrate 11 and formed in an arc shape along the peripheral edge of each injection port 13 in the surface of the first substrate 11, and a slit 22 formed in the protruding portion 21. These identification marks 20 are each provided for identifying the position of the corresponding microchannel 16 in the plane direction of the plate 10 by the difference in the position of the slit 22 formed in the protruding portion 21.

Describing with reference to FIG. 8, in the identification mark 20 relating to the microchannel 16 located on the left side, the slit 22 is formed at a position on the left side in the protruding portion 21 in the drawing to extend in the radial direction of the opening of the injection port 13. Also, in the identification mark 20 relating to the microchannel 16 located at the center, the slit 22 is formed at a position on the upper side in the protruding portion 21 in the drawing to extend in the radial direction of the opening of the injection port 13. Also, in the identification mark 20 relating to the microchannel 16 located on the right side, the slit 22 is formed at a position on the right side in the protruding portion 21 in the drawing to extend in the radial direction of the opening of the injection port 13. In this way, the position of the microchannel 16 relating to an identification mark 20 in the plane direction of the plate 10 is identified by the difference in the position of the slit 22 formed in the protruding portion 21 of the identification mark 20, and consequently, the microchannel 16 is distinguished from the microchannel 16 relating to another identification mark 20.

Figure 11:
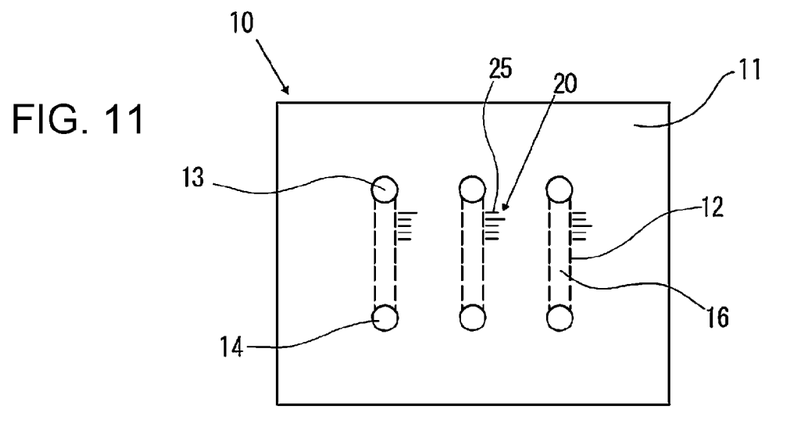
FIG. 11 is a plan view illustrating another modification of the plate of the present invention.
Figure 12:
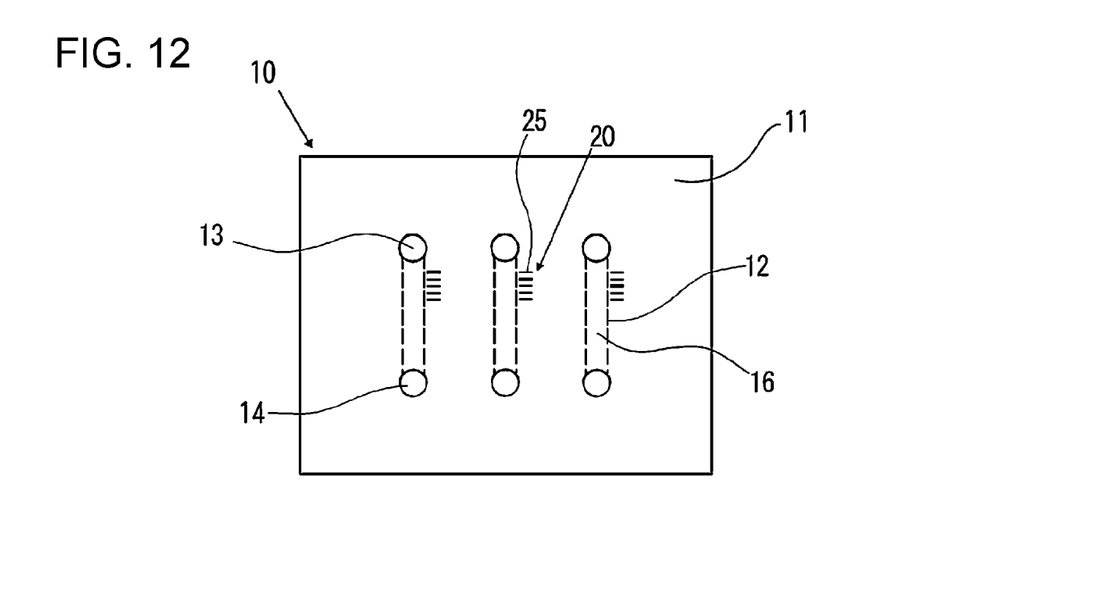
FIG. 12 is a plan view illustrating still another modification of the plate of the present invention.

Alternatively, as illustrated in FIGS. 11 and 12, an identification mark 20 may be formed by a figure including a plurality of line segments 25 arranged in parallel along the microchannel 16. Regarding an identification mark 20 illustrated in FIG. 11, one line segment 25 is longer than the other line segments 25, and the position of the corresponding microchannel 16 in the plane direction of the plate 10 is identified by the difference in the position of the long line segment 25. Alternatively, regarding an identification mark 20 illustrated in FIG. 12, one line segment 25 is thicker than the other line segments 25, and the position of the corresponding microchannel 16 in the plane direction of the plate 10 is identified by the difference in the position of the thick line segment 25.

Alternatively, when an identification mark 20 is formed by a figure including a plurality of line segments, the position of the corresponding microchannel 16 in the plane direction of the plate 10 can be identified by a binary number in which a long line segment or a thick line segment is 1 and the other line segments are 0.

(2) In the plate 10 of the present invention, it is not essential that the second substrate 15 is transparent and may be semitransparent or opaque.

(3) In the first embodiment and the third embodiment, the identification mark 20 is formed in or on the outer surface of the first substrate 11. However, the identification mark 20 may be formed in or on a surface of the first substrate 11 to be bonded to the second substrate 15, a surface of the second substrate 15 to be bonded to the first substrate 11, or both of these surfaces.

REFERENCE SIGNS LIST 10 plate
11 first substrate
12 channel forming groove
13 injection port
14 discharge port
15 second substrate
16 microchannel
17 source channel
18 branch channel
20 identification mark
21 protruding portion
22 slit
23 grid FIG.
24 opaque area
25 line segment
80 plate
81 first substrate
82 injection port
83 discharge port
85 second substrate
86 microchannel

The invention claimed is:

1. A plate having microchannels therein, comprising:
at least an identification mark for identifying a relative position of a corresponding one of the microchannels in a plane direction of the plate,
wherein the plate includes a first substrate in which a channel forming groove for forming the microchannels is formed and a second substrate stacked on the first substrate, the first substrate and the second substrate being bonded to each other, and the first substrate is made of a transparent synthetic resin, and the first substrate is provided with an injection port through which a sample is injected and an exhaust port through which the sample is discharged,
wherein a weld line is formed through injection molding in the first substrate, and the weld line is formed by uniquely extending from opening edges of the injection port or the discharge port toward a peripheral edge of the first substrate, and the identification mark for identifying a relative position of a corresponding one of the microchannels is made by the weld line.

2. The plate according to claim 1, wherein the microchannel includes a plurality of microchannels formed independently from each other, and the identification mark is formed for each of the microchannels.

3. The plate according to claim 1, wherein the microchannel includes a source channel communicating with an injection port through which a sample is injected and a plurality of branch channels communicating with the source channel, and the identification mark is formed for each of the source channel and the branch channels.

4. The plate according to any one of claims 1 to 3, wherein the identification mark is formed in an area near the microchannel or an area overlapping with the microchannel when seen in a plan view.

5. The plate according to any one of claims 1 to 3, wherein the synthetic resin is a cycloolefin resin.

6. The plate according to claim 4, wherein the synthetic resin is a cycloolefin resin.

7. The plate according to claim 1, wherein the microchannels formed in the plate flows a liquid sample containing the sample to be observed under a microscope at a magnification level, and the identification mark for identifying the relative position of a corresponding one of the microchannels with respect to others of the microchannels in the plate while observing the sample without reducing the magnification level of the microscope.

* * * * *